United States Patent [19]

Weiss et al.

[11] Patent Number: 5,677,543
[45] Date of Patent: Oct. 14, 1997

[54] DISSOLVED METHYLLITHIUM-CONTAINING COMPOSITION FOR USE IN SYNTHESIS REACTIONS

[75] Inventors: Wilfried Weiss, Oberursel; Peter Rittmeyer, Sulzbach; Ute Emmel, Frankfurt am Main, all of Germany

[73] Assignee: Metallgesellschaft AG, Frankfurt am Main, Germany

[21] Appl. No.: 499,547

[22] Filed: Jul. 7, 1995

[30] Foreign Application Priority Data

Jul. 9, 1994 [DE] Germany ............ 44 24 222.0

[51] Int. Cl.$^6$ .................................... C09K 3/00
[52] U.S. Cl. ................... 252/182.12; 252/182.3
[58] Field of Search .................. 252/182.3, 182.12

[56] References Cited

U.S. PATENT DOCUMENTS

| | | | |
|---|---|---|---|
| 4,976,886 | 12/1990 | Morrison et al. | 252/182.3 |
| 5,095,129 | 3/1992 | Ottow et al. | 552/510 |
| 5,100,575 | 3/1992 | Hatch et al. | 252/182.3 |
| 5,171,467 | 12/1992 | Mehta et al. | 252/182.3 |
| 5,523,447 | 6/1996 | Kamienski et al. | 260/655 R |

FOREIGN PATENT DOCUMENTS 0285374  10/1988  European Pat. Off. .

*Primary Examiner*—Edward A. Miller
*Attorney, Agent, or Firm*—Felfe & Lynch

[57] ABSTRACT

Disclosed is a dissolved methyllithium-containing composition for use in synthesis reactions (synthesis composition) and processes of preparing the composition. In the sythesis composition the methyllithium is contained in a solvent of the general formula (I)

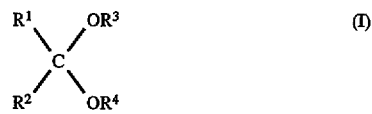

wherein independently $R^1$ and $R^2$ are a hydrogen, methyl or ethyl residue and $R^3$ and $R^4$ are a methyl or ethyl residue. To prepare the methyllithium-containing synthesis composition of the invention lithium powder or granular lithium is dispersed in a solvent having the general formula I, methyl halide is added at a controlled rate, the reaction temperature is maintained in the range of from 0° to 60° C., and the resulting lithium halide is separated from the methyllithium solution.

13 Claims, 3 Drawing Sheets

DISSOLVED METHYLLITHIUM-CONTAINING COMPOSITION FOR USE IN SYNTHESIS REACTIONS

BACKGROUND OF THE INVENTION

This invention relates to a new composition for synthesis reactions (synthesis composition), which contains dissolved methyllithium, and to process of preparing said composition.

Methyllithium is used as a reagent in the preparation of pharmaceutical products, such as vitamin derivatives or steroid derivatives, and in special synthesis stages, such as carbene-type reactions for preparing allenes and alkoxycyclopropanes, methylating reactions for preparing alkenyllithium compounds and steroidal alkenyl compounds, reducing reactions involving various transition metal halides, such as $PdCl_2$ to form $Pd(O)$, the preparation of methyllithium cuprates for use in 1,4-conjugated additions or to prepare other organo-metallic compounds, such as $Me_2Mg$, $MeTi(NEt_2)_3$, $Me_3Al$, $Me_3As$ or $Me_3Ga$.

Methyllithium is commercially available as an about 5% solution in diethyl ether or as an about 6% solution in diethyl ether, which solution contains about 10% lithium bromide as a complexing stabilizer. The usefulness of the commercially available forms of methyllithium is limited because of the presence of diethyl ether which has a low flash point. Other ethereal solutions of methyllithium have no commercial significance because, on the one hand, they contain methyllithium only in a very low concentration (about 3 wt.-%) and, on the other hand, their stability is inadequate (e.g., in THF or glycol ethers). On the other hand, methyllithium is insoluble in hydrocarbons and aromatic compounds. A certain solubility in aromatic compounds can be achieved if the methyllithium-THF complex is used (up to 3.74% by weight). For instance, the documents EP-A-0 285 374 and U.S. Pat. No. 5,171,467 disclose alkyllithium compounds in aromatic hydrocarbons, which compounds are stabilized by a content of a Lewis base, such as tetrahydrofuran, and lithium halides. Since such solutions tend to be decomposed due to the metalization of the aromatic compounds, dialkylmagnesium compounds are added so that the content of active lithium compounds is decreased to 2.6% by weight and the reactivity is influenced by the presence of dialkylmagnesium compounds.

It is an object of the invention to provide a dissolved methyllithium-containing composition for use in synthesis reactions (synthesis composition), which has a high stability in storage and a higher content of methyllithium in solution.

THE INVENTION

Figure 1:
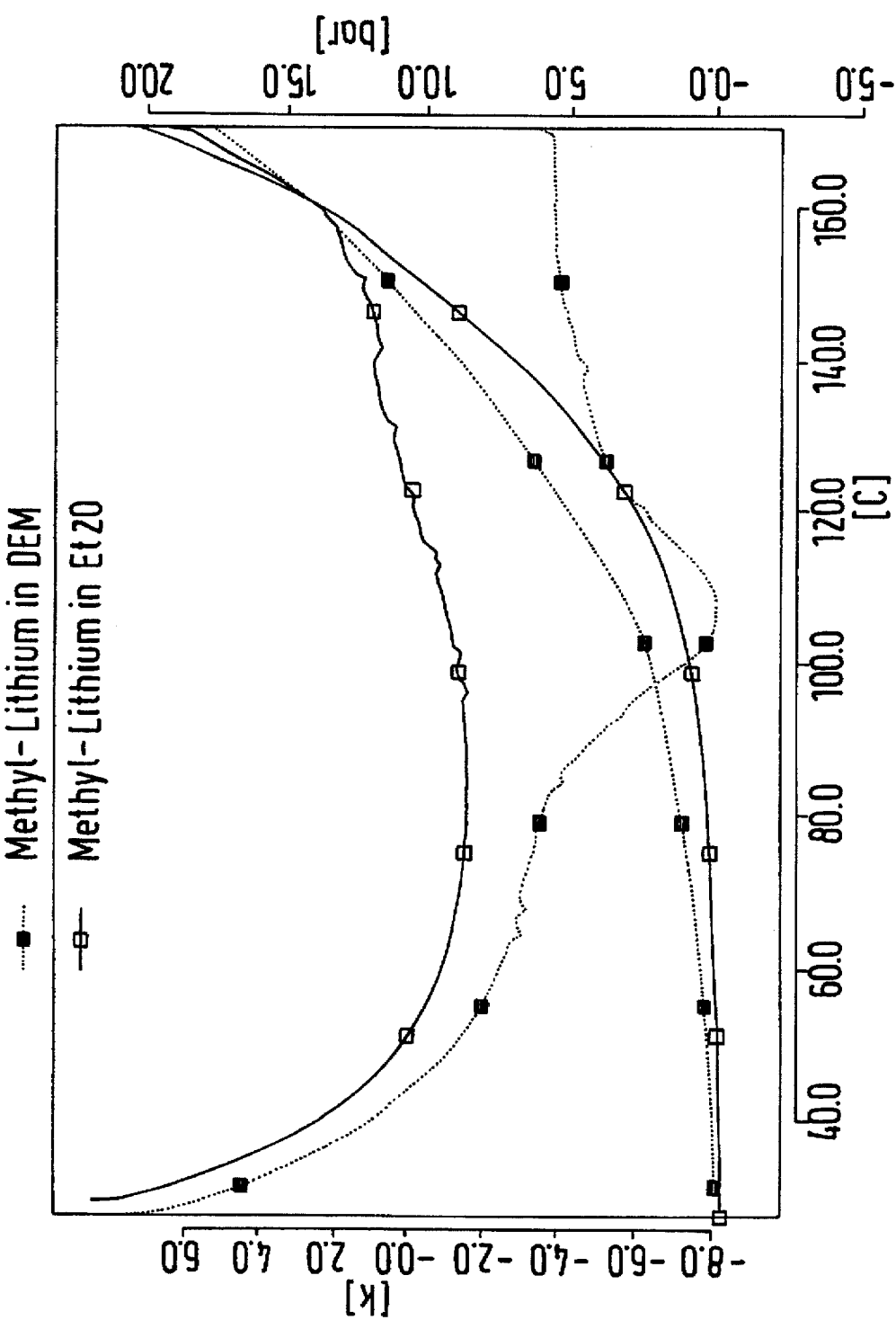
FIG. 1 illustrates a comparison of the dynamic stability curves determined by thermogravimetry of a solution of methyllithium in diethyl ether and of a solution of methyllithium in diethoxymethane ("DEM")
Figure 2:
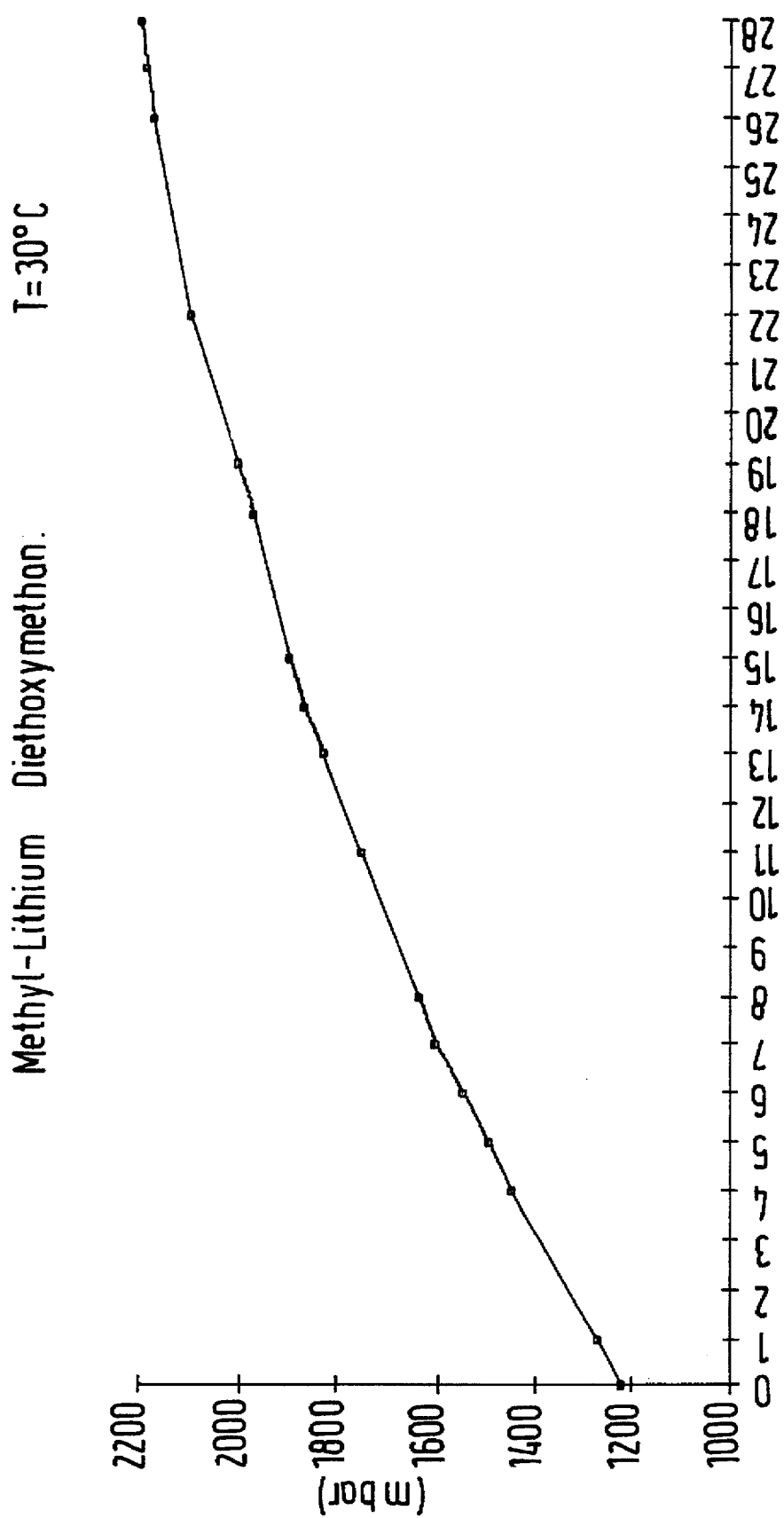
FIGS. 2 and 3 represent the stability of in storage of methyllithium in DEM and of a solution of methyllithium and lithium bromide in DEM at 30° C.
Figure 3:
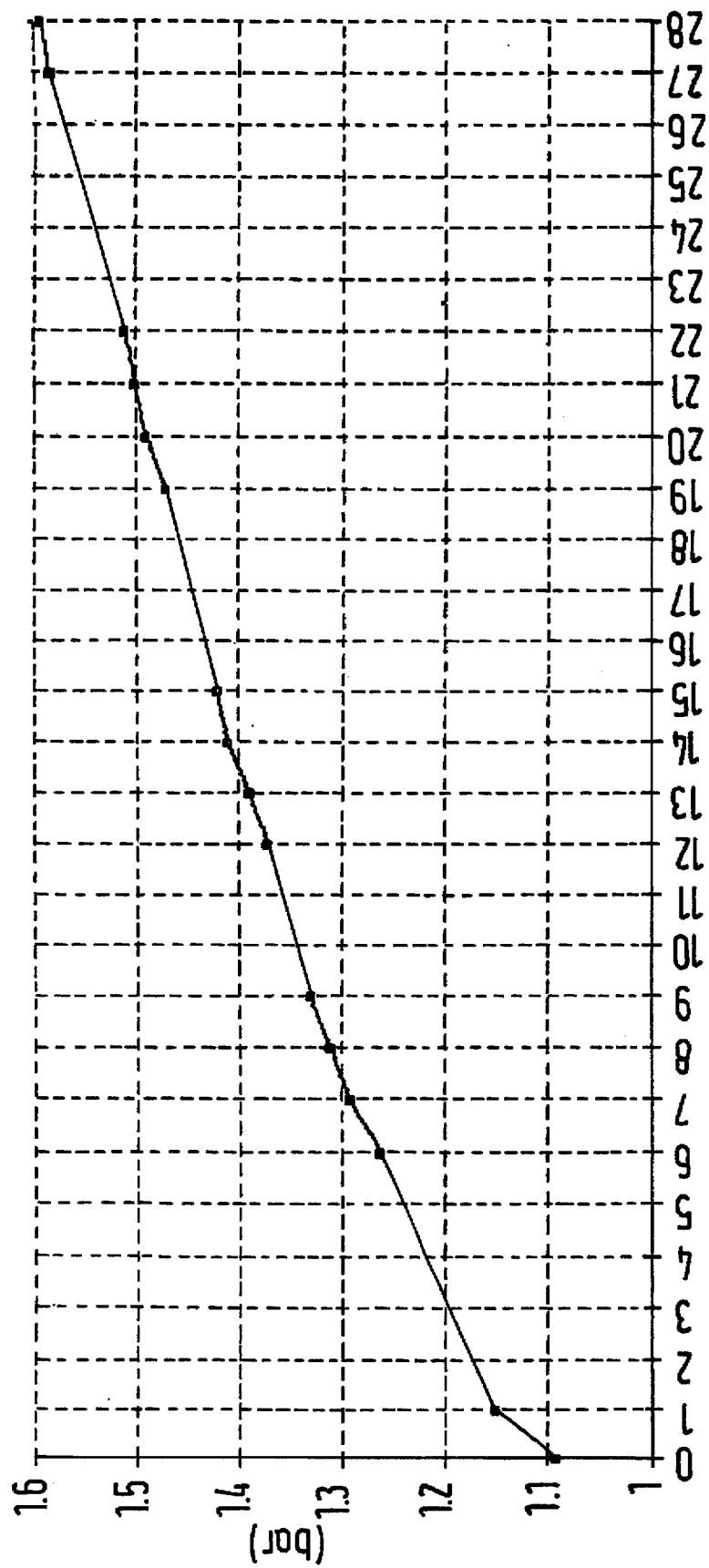

The present invention is in a composition in which the methyllithium is contained in a solvent of the general formula (I)

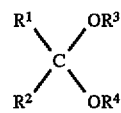

wherein independently $R^1$ and $R^2$ are a hydrogen, methyl or ethyl residue and $R^3$ and $R^4$ are a methyl or ethyl residue. The composition is useful for synthesis stages and reactions. It has surprisingly been found that at storage temperatures up to room temperature a solution of methyllithium in a solvent having the general formula I will not exhibit significant changes of its active base content within 100 days and that even during a storage at higher temperatures there will be only a gradual decomposition, which is distinctly related to the ambient temperature.

For special stereospecific syntheses, a synthesis composition is provided which contains also lithium bromide or lithium iodide. Diethoxymethane is preferably used as a solvent for the methyllithium in the synthesis composition. In a further embodiment of the invention the solution contains a methyllithium-diethoxymethane complex, in which methyllithium and diethoxymethane are present in a mole ratio from 1:0.5 to 1:2.0. Another methyllithium-containing synthesis composition in accordance with the invention is a solution of a methyllithium-diethoxymethane complex in a solvent of the general formula I and/or in a hydrocarbon, preferably in an aromatic hydrocarbon, such as toluene.

The dissolved methyllithium-containing synthesis composition is prepared in accordance with the invention in that a) lithium powder or granular lithium is dispersed in a solvent having the general formula I and methyl halide is added at a controlled rate, b) the reaction temperature is kept in the range from 0° to 60° C. and c) the resulting lithium halide is separated from the methyl-lithium solution.

The stoichiometric amount of methyl halide is preferably added at a controlled rate to the dispersion of lithium powder in diethoxymethane over 2 to 6 hours while the reaction temperature is kept in the range from 15° to 50° C.

A special synthesis composition for stereochemical reactions is obtained by adding up to 10% by weight lithium bromide or lithium iodide.

The process of the invention can be used to prepare synthesis compositions which contain 5 to 10% methyllithium in solution. The methyllithium solution of the invention has a high stability and a relatively high concentration thus providing good results when used in the known synthesis processes.

The invention will be explained more in detail in the following examples.

EXAMPLE 1

22.2 g (3200 mmols) lithium powder in 350 g diethoxymethane (DEM) are provided in a jacketed reactor at an internal temperature T(i) of 35° C. and 80.0 g (1585 mmols) methyl chloride are added over 5 hours. The reaction heat is dissipated through the jacket. After an after reaction time of 30 minutes the reacted suspension is filtered to provide a colorless filtrate that contains 3.69 mmols/g methyllithium.

EXAMPLE 2

Example 1 is repeated but granular lithium in DEM is used rather than lithium powder and at an internal temperature T(i) of 25° C. the methyl chloride is added over 315 minutes. After an after reaction time of 30 minutes the suspension is filtered through a G4 frit. 368 g of a clear, colorless solution are obtained, which contains 3.86 mmols/g methyllithium.

CONTROL EXAMPLE 1

Example 2 is repeated with the difference that the reaction is effected in 352 g diethyl ether and 83.8 g (1660 mmols) methyl chloride are added over 395 minutes. After an after reaction time of 30 minutes and filtration, 341 g of a clear, colorless solution of 4.113 mmols/g methyllithium in diethyl ether are obtained.

EXAMPLE 3

306.5 g of a solution of methyllithium in DEM, which solution has a total base content of 3.55 mmols/g, are provided in a reaction vessel at 25° C. 30 g (345 mmols) lithium bromide are added in 5-g portions. A cloudy suspension is obtained, which is filtered to provide 329 g of a clear, colorless filtrate that has a total base content of 3.24 mmols/g. The solution is found to contain 7.2% methyllithium, 8.25% lithium bromide, and 0.98% lithium chloride. The resulting solution is stored at room temperature for 19 days. Thereafter the solution is found to have a total base content of 3.20 mmols/g and an active base content of 3.00 mmols/g. This corresponds to a mean decomposition rate at 20° C. of about 0.05% methyllithium per day.

EXAMPLE 4

170 g of a solution of 550 mmols methyllithium in diethoxymethane are diluted with 200 g toluene. Surplus diethoxymethane is removed from that solution in a vacuum at room temperature until the presence of a methyllithium-DEM complex is indicated by a constancy of pressure.

| p ~ 15 mbars | DEM:methyllithium ~ 2.0:1 |
| p ~ 10 mbars | DEM:methyllithium ~ 1.5:1 |
| p ~ 5 mbars | DEM:methyllithium ~ 1.0:1 |
| p ~ oil pump vacuum | DEM:methyllithium ~ 0.5:1 |

In each case the cloudy toluenic solution of methyllithium in dioxymethane is filtered and the solubility is determined.

| Methyllithium:DEM | |
|---|---|
| | 1:2.0 = 1.54% |
| | 1:1.5 = 1.45% |
| | 1:1.0 = 1.00% |
| | 1:0.8 = 0.25% |

It will be understood that the specification and examples are illustrative but not limitative of the present invention and that other embodiments within the spirit and scope of the invention will suggest themselves to those skilled in the art.

What is claimed is:

1. A composition comprising methyllithium in a solvent of the general formula (I)

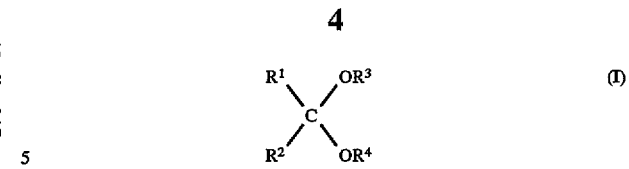

wherein independently $R^1$ and $R^2$ are a hydrogen, methyl or ethyl residue and $R^3$ and $R^4$ are a methyl or ethyl residue.

2. The composition of claim 1 further comprising at least one of lithium bromide and lithium iodide.

3. The composition of claim 1 wherein the solvent is diethoxymethane.

4. The composition of claim 1 wherein the solution contains a methyllithium-diethoxymethane complex in which methyllithium and diethoxymethane are present in a mole ratio of from 1:0.5 to 1:2.0.

5. The composition of claim 1, wherein a methyllithium-diethoxymethane complex is dissolved in a solvent of the general formula I and an aromatic hydrocarbon.

6. The composition of claim 5 wherein the aromatic hydrocarbon is toluene.

7. A process of preparing a methyllithium containing composition of claim 1 comprising:

a) dispersing lithium powder or granular lithium in a solvent of the general formula (I)

wherein $R^1$ and $R^2$ are independently a hydrogen, methyl or ethyl residue and $R^3$ and $R^4$ are a methyl or ethyl residue;

b) adding methyl halide at a controlled rate;

c) reacting the lithium powder or granular lithium with the methyl halide at a reaction temperature in the range of 0° to 60° C. to produce lithium halide; and d) separating the lithium halide from the methyllithium solution.

8. The process of claim 7 wherein the metal halide is added in a stoichiometric amount at a controlled rate to the dispersion of lithium powder or granular lithium over 2 to 6 hours while the reaction temperature is within the range of from 15° to 50° C.

9. The process of claim 7, further comprising adding up to 10% lithium bromide or lithium iodide.

10. The composition of claim 4 wherein a methyllithium-diethoxymethane complex is dissolved in a solvent of the general formula I with an aromatic hydrocarbon.

11. The process of claim 7 wherein the solvent also contains an aromatic hydrocarbon.

12. The process of claim 7 wherein the solution contains a methyllithium-diethoxymethane complex in which methyllithium and diethoxymethane are present in a mole ratio of from 1:0.5 to 1:2.0.

13. The process of claim 11 where the aromatic hydrocarbon is toluene.

* * * * *

UNITED STATES PATENT AND TRADEMARK OFFICE
CERTIFICATE OF CORRECTION

PATENT NO. : 5,677,543
DATED : October 14, 1997
INVENTOR(S) : Weiss et al.

It is certified that error appears in the above-identified patent and that said Letters Patent is hereby corrected as shown below:

In column 2, line 36, after "60°C." add -- , --.

In column 2, line 60, following "after" add a hyphen, -- - --.

In column 3, line 2, change "after reaction" to one word -- afterreaction --.

In column 3, line 12, change "4,113" to -- 4.113 --.

Signed and Sealed this

Fifteenth Day of June, 1999

Attest:

Q. TODD DICKINSON

*Attesting Officer*   *Acting Commissioner of Patents and Trademarks*